(12) United States Patent
Berthiaume et al.

(10) Patent No.: US 8,926,588 B2
(45) Date of Patent: Jan. 6, 2015

(54) STEERABLE DELIVERY CATHETER

(75) Inventors: William Berthiaume, Santa Rosa, CA (US); Don Tran, Novato, CA (US); Maria Valdovinos, Santa Rosa, CA (US); Brent Locsin, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 754 days.

(21) Appl. No.: 13/176,193

(22) Filed: Jul. 5, 2011

(65) Prior Publication Data

US 2013/0012925 A1    Jan. 10, 2013

(51) Int. Cl.
*A61M 25/00* (2006.01)
*A61M 25/01* (2006.01)
*A61F 2/966* (2013.01)
*A61F 2/24* (2006.01)
*A61F 2/01* (2006.01)
*A61B 5/0215* (2006.01)
*A61N 1/372* (2006.01)

(52) U.S. Cl.
CPC ............ *A61M 25/0147* (2013.01); *A61F 2/966* (2013.01); *A61M 25/0141* (2013.01); *A61F 2/2466* (2013.01); *A61M 25/0136* (2013.01); *A61F 2002/011* (2013.01); *A61M 2025/0161* (2013.01); *A61B 5/0215* (2013.01); *A61N 1/37205* (2013.01)
USPC ........... 604/528; 604/533; 604/534; 604/535; 604/536; 604/95.01

(58) Field of Classification Search
CPC ...................... A61M 25/0141; A61M 25/0147
USPC ............ 604/528, 529, 533–536, 93.01, 95.01
See application file for complete search history.

(56) References Cited

U.S. PATENT DOCUMENTS

| | | | |
|---|---|---|---|
| 2,007,626 A | | 7/1935 | Waring |
| 3,334,629 A | | 8/1967 | Cohn |
| 4,588,395 A | | 5/1986 | Lemelson |
| 5,147,379 A | | 9/1992 | Sabbaghian et al. |
| 5,372,587 A | * | 12/1994 | Hammerslag et al. ...... 604/95.04 |
| 5,397,321 A | * | 3/1995 | Houser et al. .................. 606/41 |
| 5,601,568 A | | 2/1997 | Chevillon et al. |
| 5,674,271 A | * | 10/1997 | Denker ........................ 607/119 |
| 5,743,874 A | * | 4/1998 | Fischell et al. ............. 604/103.1 |
| 6,607,496 B1 | * | 8/2003 | Poor et al. .................... 600/585 |
| 6,773,446 B1 | | 8/2004 | Dwyer et al. |

(Continued)

FOREIGN PATENT DOCUMENTS

| | | |
|---|---|---|
| EP | 0119688 | 9/1984 |
| WO | WO02/22196 | 3/2002 |

*Primary Examiner* — Quynh-Nhu H Vu
*Assistant Examiner* — Brandy S Lee

(57) ABSTRACT

A steerable delivery catheter includes an outer sheath with a housing disposed at a distal end thereof to define a chamber for a medical device, the chamber having an open distal end and a proximal inner shelf. An inner shaft is slidably disposed within the sheath and has an abutment attached to the distal end of the shaft, the abutment being slidably contained within the chamber. During navigation of the catheter, when the inner shaft is tensioned the abutment engages the shelf to apply a compressive force to the sheath to selectively deflect a distal region of the catheter. When the catheter has been navigated to the deployment site the sheath is withdrawn while the abutment maintains the medical device in place as it is deployed. A delivery method also is disclosed.

20 Claims, 5 Drawing Sheets

(56) References Cited

U.S. PATENT DOCUMENTS 7,371,248 B2 5/2008 Dapolito et al.
2002/0007190 A1* 1/2002 Wulfman et al. ............. 606/167
2005/0080356 A1* 4/2005 Dapolito et al. ............. 600/585
2006/0004305 A1* 1/2006 George et al. ................ 600/593

* cited by examiner

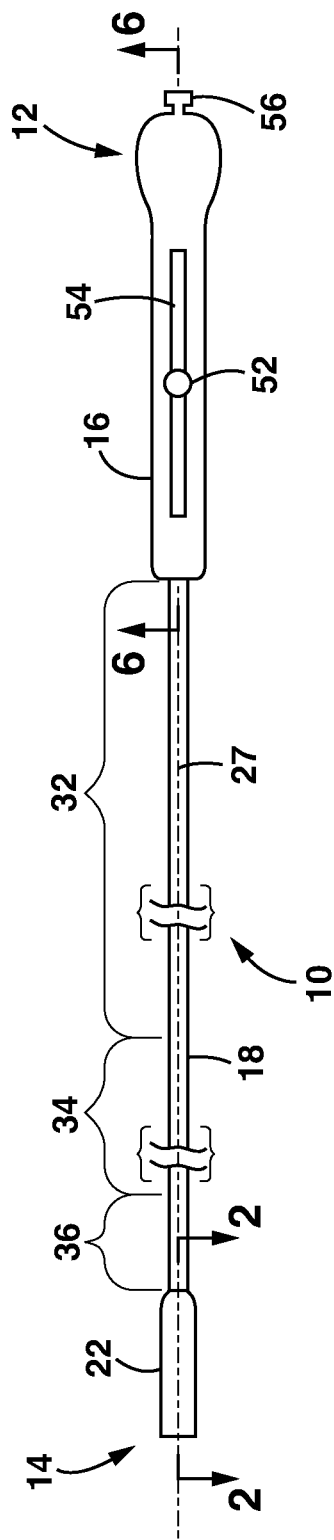
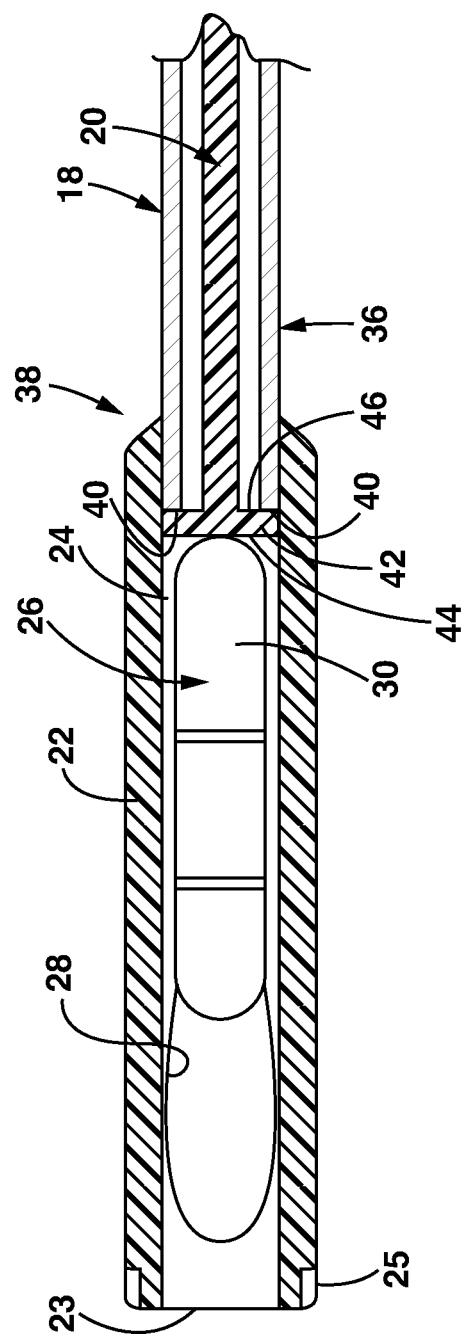

STEERABLE DELIVERY CATHETER

FIELD

This invention relates generally to steerable catheters capable of delivering a medical device to and deploying the device at a selected location in a body lumen.

BACKGROUND

Among the medical catheters commonly used to access vascular and other locations within the body and to perform various functions at those locations are those adapted to deliver and deploy medical devices such as stents, vascular filters, sensors and pacing devices to selected targeted sites in the body. Such medical devices typically are releasably carried at the distal region of the delivery catheter in a state ready to be deployed by the catheter after the distal end of the catheter has been navigated to and positioned at the target deployment site. In many cases, such as those involving cardiovascular vessels, the path to the deployment site may be tortuous and may present conflicting design considerations requiring compromises between dimensions, flexibilities, material selection, operational controls and the like. One such example is presented in connection with accessing the pulmonary artery through the right side of the heart that includes a path from access through the femoral vein, a path that requires multiple 180 degree bends.

Typically the advancement of the catheter within the patient is monitored fluoroscopically to enable the clinician to manipulate the catheter to steer and guide its distal end through the patient's vessels to the target site. In one common technique, a steerable guide wire is used to access the target site with the catheter being advanced over the guidewire to locate the distal end of the catheter at the target site. Other catheters have been designed to omit the guide wire and, instead, rely on a catheter construction in which the catheter itself may be steerable by providing one or more pull wires through the catheter by which the distal region of the catheter can be bent or deflected. By bending the distal end of the catheter and constructing the catheter to transmit controllably rotational movement from the proximal end to the distal end, the clinician may controllably steer the end of the catheter through bends in the vasculature. As with the wire-guided devices, when the distal end of the catheter is positioned at the deployment site, the catheter is operated to deploy the device Although it is desirable, in many instances, to use a catheter with a small diameter to facilitate navigation through tortuous vasculature, small diameter catheters present various design difficulties resulting from competing considerations, resulting in design trade-offs. In general, incorporating more functions into a catheter will tend to result in a larger diameter catheter in order to contain the components required for the functions. For example, a wire-guided catheter may require a lumen in the catheter to contain the guide wire. If one or more wires is required to operate the deployment mechanism, that may require additional space within the catheter. In catheters that omit guide wires and, instead, are themselves steerable, the typical pull wire(s) and the connection to the catheter body may add to the size of the catheter as well as complexities in construction of the catheter.

It would be desirable to provide a delivery catheter for medical devices that embodies a simple construction and in which the number of components for navigating the catheter and deploying the medical device is minimized. It is among the objects of the invention to provide such delivery catheters and methods for deploying medical devices.

SUMMARY OF THE INVENTION

The invention includes an elongate catheter body having proximal and distal ends. The catheter body includes an outer tubular sheath having a chamber at its distal end to contain the implantable medical device, the distal end of the chamber being defined by an open distal port through which the medical device may be deployed. The catheter also includes an inner shaft that extends through and is movable longitudinally within the outer sheath. An abutment having distal and proximal surfaces is secured to the distal end of the inner shaft, with its distal surface defining the closed proximal end of the chamber. The outer sheath, in its distal region adjacent the chamber, has a shelf against which the proximal face of the abutment may bear to apply a longitudinally compressive force to the outer tubular sheath when the inner shaft is drawn proximally within the outer sheath. The compressive force and the flexibilities of the distal regions of the inner shaft and the outer sheath are such that the compressive force will cause the distal region of the sheath to bend longitudinally to a curved shape that can be selectively directed by rotation of the proximal end of the catheter. The degree of longitudinal bending is a function of the amount of compression applied to the outer sheath. When the chamber containing the medical device has been navigated to and positioned at the target site, the outer sheath is retracted proximally to progressively withdraw the chamber from about the medical device, thus deploying the device. During retraction of the outer sheath the position of the medical device at the target site is maintained by engagement of its proximal end with the distally facing surface of the abutment. A handle to which the proximal ends of each of the outer sheath and inner shaft are connected facilitates catheter rotation and the relative longitudinal positioning of the inner shaft and the outer sheath.

The invention also may include an arrangement by which the position of the partially deployed medical device can be reconsidered by the clinician and, if desired, the medical device can be recaptured into the catheter. Such recapture enables redeployed in another location or orientation or to enable the device to be removed without deployment.

DRAWINGS

The advantages and features of the invention will be appreciated more fully from the following description with reference to the accompanying drawings in which:

FIG. 1 is a fragmented, diagrammatic side view of the catheter

FIG. 2 is a enlarged longitudinal section of the distal region of the catheter as seen along the lines 2-2 of FIG. 1;

DESCRIPTION

Figure 3:
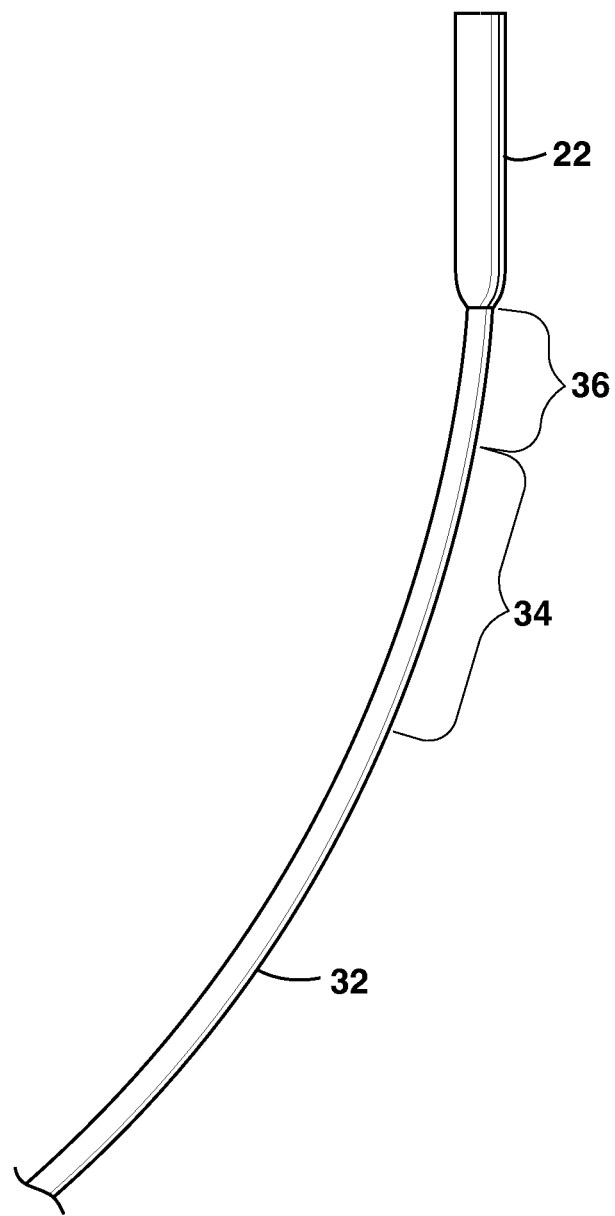
FIGS. 3-5 are representative illustrations of the degree of deflection of the distal regions of the catheter under the influence of increasing compressive loads.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The drawings illustrate delivery catheters adapted to deliver relatively large diameter cardiovascular medical devices such as, for example, wireless pressure sensing devices and percutaneously placeable leadless pacing systems. It should be understood, however, that the principles of the invention may be incorporated in delivery catheters for delivering other, smaller devices such as stents and filters for distal embolic protection among others.

As shown in FIG. 1, one embodiment of the delivery catheter 10 has a proximal end 12 and a distal end 14. A handle 16 preferably is disposed at the proximal end for controlling operation of the catheter. The catheter has a catheter body that includes an outer tubular sheath 18. An inner shaft 20 (FIG. 2) extends through the lumen of outer sheath 18, sheath 18 and inner shaft 20 being movable longitudinally relative to each other. A housing 22 adapted to contain a medical device in a low profile configuration is attached to and extends distally from the distal end of sheath 18. Device housing 22 defines a chamber 24 having an open distal port 23 that may be identifiable fluoroscopically by a radiopaque marker band 25 at the distal end of the housing. For ease of description, the catheter may be considered as having a linear axis 27 (FIG. 1) that extends along a direction coincident with the catheter when the catheter is straight, without bends. Linear axis 27 serves as a reference from which the arc of curvature of the deflected distal portions of the catheter may be measured. Device housing 22 may be considered to have its own linear axis that is aligned with catheter axis 27 when the catheter is straight.

Chamber 24 is adapted to contain any of a variety of medical devices to be deployed at a target location reachable by the navigable catheter. The diameter of the housing will depend on the dimensions of the medical device when in a collapsed, low profile configuration. In the event that the housing diameter is relatively large in relation to the outer sheath diameter, and the catheter introducer sheath with haemostatic valve (not shown) is large enough to accommodate the housing, the outer sheath of the catheter may be provided with a valve relief 55 (FIGS. 7-9) to take up the annular gap between the inside diameter of the introducer sheath and the outside diameter of outer sheath 18. Valve relief 55 is slidable, but in a close fit about outer sheath 18, to minimize backbleeding between the valve relief and outer sheath.

By way of example, chamber 24 may contain a sensor assembly 26 that includes one or more fixation members 28 affixed to a sensor 30. Fixation member 28 may be self expandable from a low profile configuration to an expanded configuration for engagement with a vessel wall or other tissue to perform its function. For example, in an assembly adapted to sense blood pressure in a blood vessel, the fixation member may be adapted to engage the vessel wall with forces just sufficient to maintain the assembly in place without applying forces that may cause trauma to the vessel. By way of illustration such a sensor assembly is described in further detail in U.S. patent application Ser. No. 13/090,854. It should be understood, however, that use of the invention is not limited to deployment of sensors.

As shown in FIG. 1, outer sheath 18 of the catheter includes several serially attached segments including a proximal segment 32, an intermediate segment 34 and a distal segment 36.

Housing 22 is attached to and extends distally from the distal end of distal segment 36 of outer sheath 18. In the illustrated embodiments, for a delivery device adapted to contain and deliver a pressure sensing assembly or a pacing system, the outer diameter of housing 22 may be of the order of about 24 French (0.312 inch). The segments 32, 34, 36 define a progressively flexible structure from the proximal end to the distal end of the device. In one illustrative example adapted to deliver and deploy a pressure sensor assembly in a pulmonary artery the overall length of the catheter body may be of the order of about 110 centimeters. It should be understood that the length of the catheter depends on the target site of deployment and the approach selected to reach that site.

Proximal segment 32, which is the stiffest and longest of the segments, provides column strength for "pushability" and torsional rigidity to facilitate advancement of the catheter and torque transmission from the proximal end to the distal end of the catheter to facilitate steering. The proximal segment may be formed from stainless steel braided wire or from a polymer having longitudinal stiffening elements such as braided elements, coils or stiffening wires, if desired. The handle 16 is attached at the proximal end of proximal segment 32. For a catheter intended to enter a patient's groin area and deploy a device in the pulmonary artery, proximal segment 32 may be of the order of about 100 centimeters in length and may be formed, for example, from a 72 Shore D medical grade plastic resin such as polyether block amide copolymer sold under the trademark PEBAX 7233. The outer diameter of the proximal, intermediate and distal segments may be of the order of about 0.170 inch with a wall thickness of the order of about 0.013 inches with an inner diameter of about 0.144 inch. Proximal segment 32 may include an inner braided or other reinforcement should that be desired to enhance stiffness or torque transmission. It may be noted that, in the illustrative embodiments, housing 22 is larger in diameter than the body of the catheter proximal of the housing. This is a function of the collapsed diameter of the medical device to be delivered. While with such larger diameter devices the initial percutaneous access requires passing the housing through the punctured skin and subcutaneous tissue, once the housing has been placed in the blood vessel, such as the femoral artery, then the catheter can be advanced with relatively little resistance.

Distal segment 36 is the shortest and most flexible of the catheter segments. It may be of the order of about three centimeters long and formed from more flexible, relatively soft 35 Shore D medical grade plastic resin such as polyether block amide copolymer sold under the trademark PEBAX 3533. The distal segment preferably includes a flexible braid as reinforcement. Intermediate segment 34 may be approximately ten centimeters long and has stiffness in between that of proximal and distal segments 32, 36 to serve as a transition from stiff proximal segment 32 to flexible distal segment 36. It may be formed, for example, from a 40 Shore D medical grade plastic resin such as polyether block amide copolymer sold under the trademark PEBAX 4033. The segments may be joined end-to-end by any of a variety of techniques familiar to those skilled in the art such as, for example, adhesive, heat or ultrasonic bonding.

Tubular device housing 22 may be larger in diameter than outer sheath 18 and is attached to the distal end of flexible distal segment 36 in an overlapping joint 38 to define a distally facing shelf 40 within the proximal portion of housing 22. Adhesive bonding or other suitable methods known to those skilled in the art may be used to join the housing and distal segment. Housing 22 is constructed to retain the medical device in a low profile configuration and may be made from any material suitable for that purpose. Housing 22 should be adapted to slide easily over the low profile medical device to expose and release the medical device.

Inner shaft 20 extends through the lumen of and may be longer than outer sheath 18 by an amount sufficient to permit operation as described below. Inner shaft 20 may be formed in one of a number of constructions to provide the requisite tensile strength to bend outer sheath 18 and to also provide compression strength to hold medical device 26 in position while outer sheath 18 is withdrawn during deployment. The inner shaft may be a solid or tubular structure, metallic or polymeric, or a combination of both and may have reinforcing elements such as braided or unbraided wires embedded in or attached as part of the inner shaft. The reinforcing elements, if used, may be incorporated in a manner that will bias the direction in which the catheter 10 will bend to provide a predictive direction of articulation when the inner shaft is tensioned. Such biasing elements also may be incorporated into the outer sheath 18 for the same purpose.

An abutment 42 is firmly secured to the distal end of inner shaft 20, as by adhesive, welding or other suitable means and is contained slidably within chamber 24 of the housing 22. Abutment 42 preferably is radiopaque or is provided with a radiopaque marker to enhance its visibility under fluoroscopy and provide an indication of the location of the proximal end of the chamber and medical device. Abutment 42 may be disc-shaped and has a distal face 44 that defines the proximal end of the chamber 24. Abutment 42 may be of a metal or rigid polymeric material and has a proximal face 46 that engages with shelf 40 to limit proximal movement of abutment 42 within the catheter.

When abutment 42 and shelf 40 are engaged, tension applied to inner shaft 20 is transmitted to a longitudinally compressive force in sheath 18. Longitudinal compression of outer sheath 18 causes segments 32, 34, 36 of the sheath to bend with the greatest degree of bending occurring in distal segment 36, a lesser degree of bending occurring in the intermediate, transition segment 34 and the least degree of bending occurring in proximal segment 32 as suggested in FIGS. 3-5. The degree of articulation of the catheter is controllable by varying the degree of tension applied to inner shaft 20. When the tension on the inner shaft is released, the catheter will relax and will tend to straighten under the influence of the resilience of the catheter components to the extent permitted by the body passageway through which the catheter was navigated into the deployment position. To deploy a medical device, tension is applied to outer sheath 18 to retract the sheath and housing proximally with respect to inner shaft 20 and abutment 42 to expose and release a device contained in chamber 24. Thus, the arrangement of the outer sheath 18, inner shaft 20 and abutment 42 enable deflection of the catheter tip and deployment of the medical device by a single, dual-function mechanism.

Delivery catheter 10 incorporates a construction that has relatively few components and is relatively easy to make. In contrast to steerable catheters in which one or more pull wires are attached eccentrically to the distal end of the catheter, the present invention avoids the need for a separate pull wire and does not require such a pull wire to be attached to the distal end of the catheter. Additionally, when assembling the delivery catheter it is not necessary to take care to precisely attach the inner shaft to an eccentric location to assure that the outer sheath will deflect in a particular direction. While the connection of inner shaft 20 to abutment 42 may be eccentrically located, that is not necessary to the functioning of the invention. Tensioning the inner shaft 20 to longitudinally compress the outer sheath 18 will cause the sheath to articulate as described above. If it is desired to provide a predetermined bias to the direction in which the outer sheath will bend, that may be achieved by reinforcing or stiffening selected eccentric portions of the sheath to provide the desired bias. Additionally variations in wall thickness of selected regions of the outer sheath, particularly in the distal section, may be employed for that purpose. Regardless of the direction of bending taken by outer sheath 18, catheter 10 can be aimed by rotating the catheter to the desired angular orientation. Outer sheath 18 is constructed to provide torsional rigidity to facilitate transmission of rotation from the catheter proximal end 12 to the catheter distal end 14.

Figure 4:
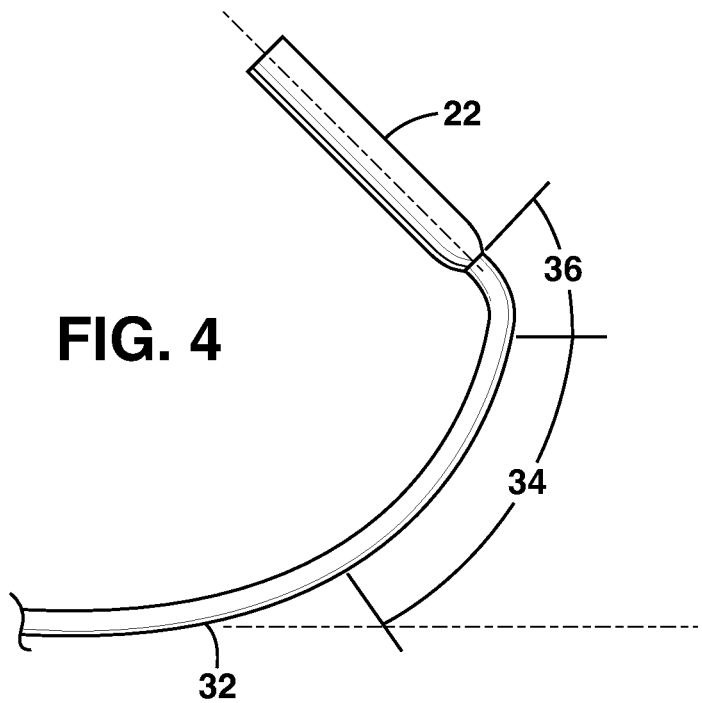
Figure 5:
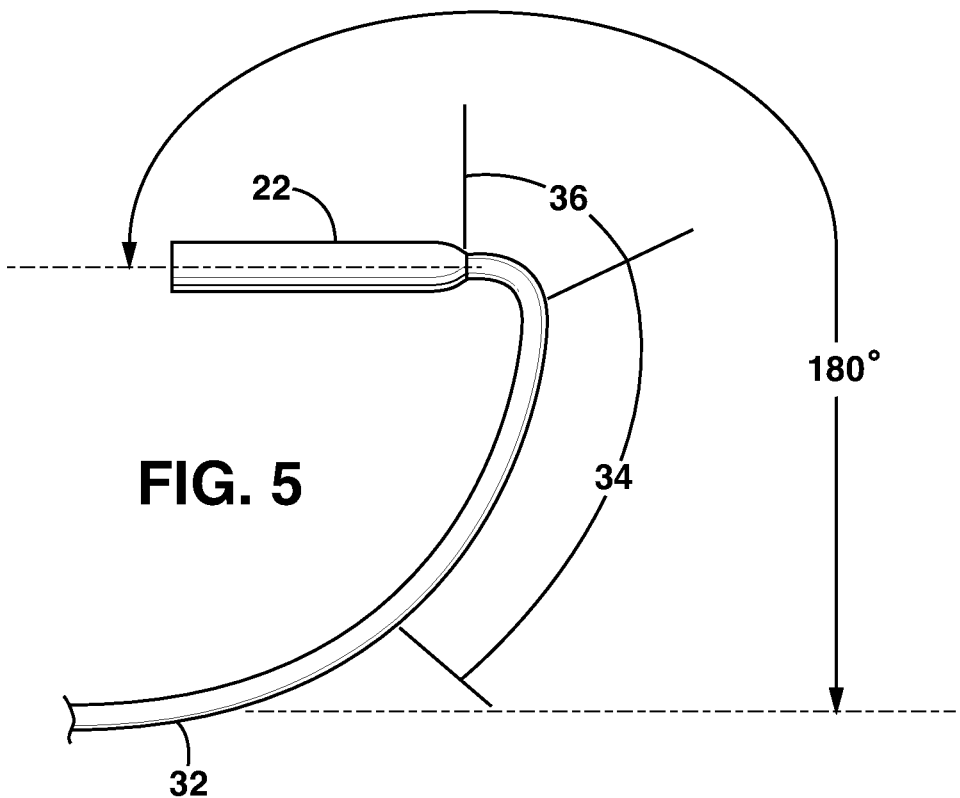

The invention enables a substantial degree of articulation. FIGS. 3-5 illustrate the relative articulation of the portions of the catheter under progressively increasing compressive load imposed on outer sheath 18 by the tensioned inner shaft 20 and abutment 42. FIG. 3 shows the degree of curvature when a relatively low level of tension is applied to the inner shaft 20. FIG. 4 shows the configuration with an increased level of tension and FIG. 5 shows the configuration with a further increased level of tension. Housing 22 is not subjected to the compressive load imposed on outer sheath 18 and remains in its straight tubular shape throughout the compressive loading on the sheath. As the compressive load increases it can be seen that housing 22 is progressively oriented at an increasing angle to linear axis 27. As seen in FIG. 5, housing 22 has been reoriented through an angle of about 180 degrees relative to linear axis 27. Thus, as shown, to the extent that proximal segment 32 may be curved away from the linear axis, it has the largest radius and least amount of curvature, intermediate segment 34 displays a greater degree of curvature with a smaller radius and distal segment 36 undergoes the greatest degree of curvature with the smallest radius. By varying the tension on inner shaft 20 and by rotating the catheter, the orientation of housing 22 can be controllably directed to facilitate steering the delivery catheter along the selected path to the deployment site.

After delivery catheter 10 has been advanced to place housing 22 at the intended target site and the clinician has determined that the medical device can be released, the position of inner shaft 20 is maintained while outer sheath 18 and housing 22 are retracted proximally to progressively expose medical device 26 and permit it to self-expand as it deploys within the vessel (see FIG. 7, discussed below). During release, the position of the medical device in the patient is maintained by engagement of its proximal end with the abutment 42 (FIG. 2). As the retraction of sheath 18 is initiated the tension on inner shaft 18 is released and the catheter is free to assume a relaxed configuration defined by the path through which the catheter was advanced to reach the target site.

Figure 6:
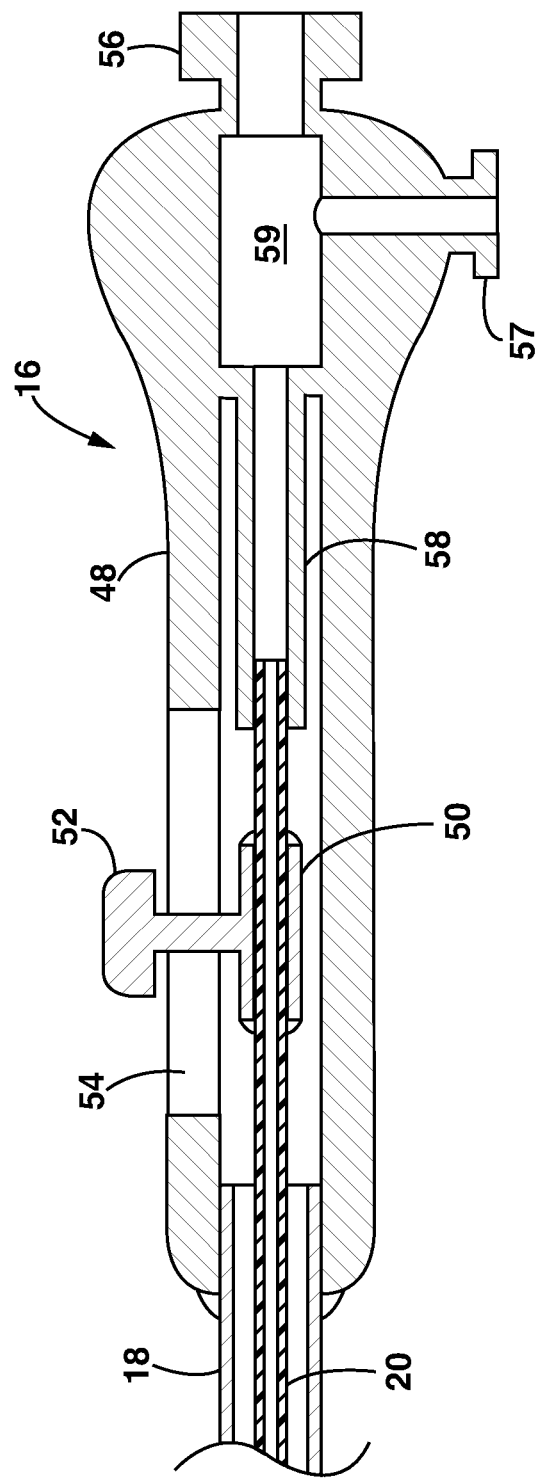
FIG. 6 is a longitudinal section of the handle portion of the catheter as seen along the line 6-6 of FIGS. 1.

Handle 16 at proximal end 12 controls the operation of the catheter. As shown in FIG. 6 handle 16 includes a housing 48 that contains a slide 50 for longitudinal sliding movement therewithin. Slide 50 has a portion that extends transversely through a longitudinal slot 54 in handle housing 48 and defines an externally accessible button 52 that may be manipulated by the clinician to move slide 50 forward or rearward. Slide 50 is attached near the proximal end of inner shaft 20 and the proximal end of outer sheath 18 is secured to housing 48. The components are arranged so that the button and slide will have a neutral position midway along slot 54 in which inner shaft 20 is not tensioned and abutment 42 is in its proximal position against shelf 40. Thus, in this arrangement the inner shaft may be tensioned to deflect the distal end of catheter 10 by retracting slide 50 relative to handle housing 48 in a proximal direction from the neutral position. Retracting handle housing 48 relative to the slide 50 in a proximal direction will maintain the position of medical device 26 in the patient's anatomy while causing sheath 18 and housing 22 to be withdrawn to deploy the medical device.

A reverse arrangement (not shown) may be employed in which inner shaft 20 is connected to housing 48 proximally of slot 54 and the proximal end of outer sheath 18 is connected to slide 50 such that it is axially movable within housing 48, resulting in a reversed mode of operation for tensioning and sheath retraction. For example, in the reverse arrangement, retracting slide 50 relative to housing 48 in a proximal direction from the neutral position will maintain the position of medical device 26 in the patient's anatomy while causing sheath 18 and housing 22 to be withdrawn to deploy the medical device.

Handle 16 may include a Tuohy-Borst type fitting 56, shown schematically in FIG. 6 and discussed in further detail below, and a side port 57 that communicates with the lumen of inner shaft 20 to enable fluid to pass through the catheter, as for flushing or other purposes. As illustrated in FIG. 6, tube 58 is fixed within housing 48 and receives the proximal end of hollow inner shaft 20 to form a sliding seal therebetween. Thus, side port 57 fluidly communicates with the lumen of inner shaft 20 via the interior of tube 58 and chamber 59 of handle housing 48. To also flush the lumen of outer sheath 18 and device housing 22, one or more ports (not shown) may be provided through the wall of inner shaft 20 generally midway along the length of the inner shaft. In this embodiment, liquid injected into side port 57 will flow through the lumen of hollow inner shaft 20 and also through the flush port in shaft 20 into the lumen of outer sheath 18. Air can thus be forced out of the distal end of inner shaft 20 and from both ends of outer sheath 18.

Figure 7:
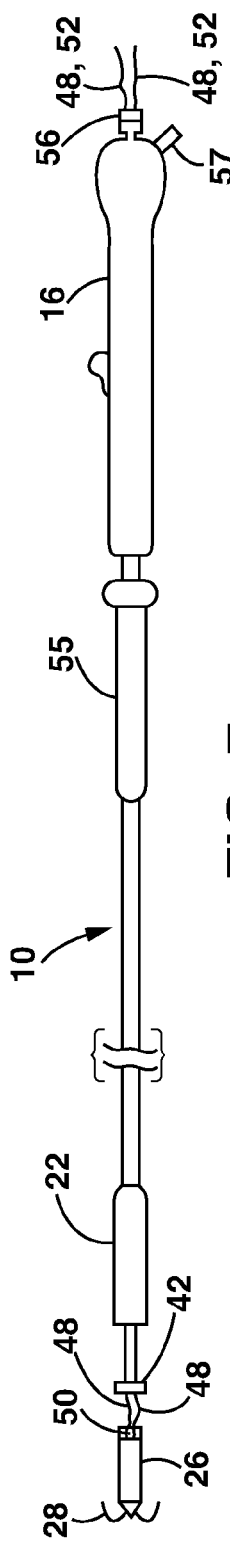
FIGS. 7-9 are diagrammatic illustrations of an embodiment showing the sequence of operation in which the medical device can be recaptured before full deployment to enable repositioning or removal.
Figure 8:
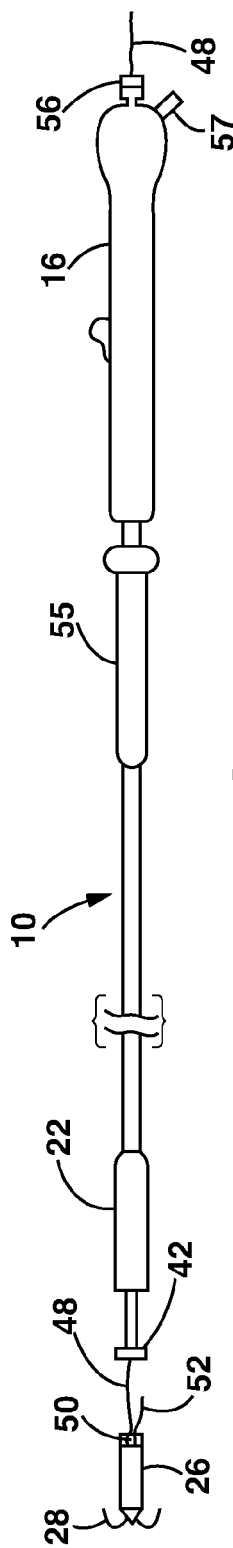
Figure 9:
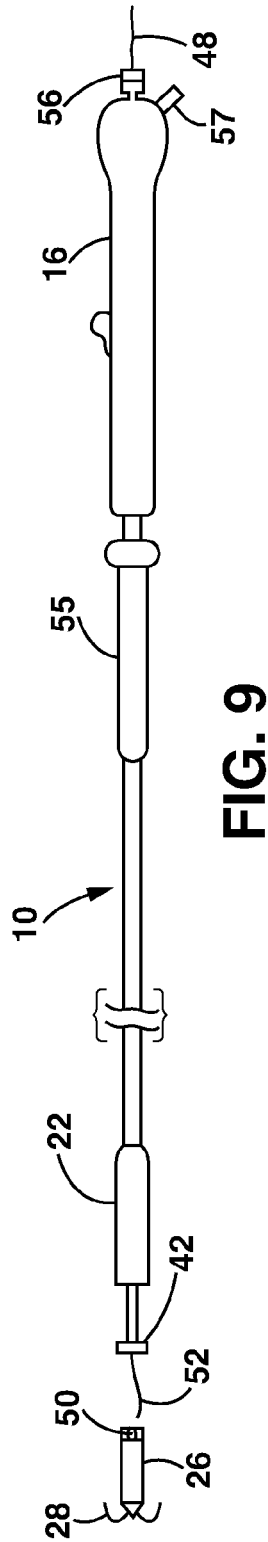

FIGS. 7-9 illustrate, diagrammatically, a modified embodiment of the invention in which partially deployed medical device 26 can be recaptured into housing 22 if it is determined that the implantable device was not deployed properly or in the correct position. Upon recapture, medical device 26 can be repositioned and redeployed or removed from the patient. In this embodiment a suture thread or wire tether 48 extends through the delivery catheter 10, preferably through the lumen of a tubular inner shaft 20, the tether being doubled to define a bight 50 at its distal end and a pair of free tails 52 that protrude from a fitting 56 at the proximal end of handle 16. Tether 48 is passed through an aperture in the medical device so that bight 50 is attached thereto. An aperture also is formed in abutment 42 to permit doubled tether 48 to pass through the abutment into chamber 24. The fitting 56 is of the type that can be adjusted to clamp or release the free tails 52, such as a Tuohy-Borst type of device having that can be twisted to grip or release the tether with a compressible element. When catheter 10 is ready to deliver medical device 26, the device will be contained in a low profile configuration in housing 22 with tether 48 extending from an aperture in the proximal end of the device and with fitting 56 tightened about tails 52 of tether 48 to lock them in place. After the catheter has been navigated to locate housing 22 at the intended deployment site, the slide in the handle is operated to withdraw the sheath to allow the medical device to engage the vessel or other target tissue (FIG. 8). At this juncture the clinician may observe, fluoroscopically, the position and orientation of the device. If the clinician is satisfied with the device placement, fitting 56 is opened to release the grip on tether 48 and one of the tails 52 can be pulled to withdraw and unthread the tether from engagement with the aperture of medical device (FIG. 9). However, if the placement is not found to be satisfactory, then sheath 18 and capsule 22 can be advanced distally over tether 48 to recapture device 26 in chamber 24. The recapture movement will transform medical device 26 back to the low profile configuration by compressing fixation members 28 as they are drawn into chamber 24. The catheter then can be repositioned and the device redeployed or the entire assembly may be removed from the patient.

From the foregoing it will be appreciated that the invention provides a delivery catheter for a medical device that is of simplified construction with relatively few components and which is easily constructed. The catheter avoids the need for a separate guide wire to navigate the catheter or a separate pull wire to control the deflection of the distal end of the catheter. The single mechanism by which the catheter is operated controls both functions of tip deflection and deployment of the medical device. It should be understood that the foregoing description of the invention is intended only as illustrative and that other embodiments, modifications and equivalents may be apparent without departing from the principles of the invention.

We claim:

1. A steerable catheter for delivering and deploying a medical device comprising:
    an elongate tubular outer sheath having proximal and distal ends and a linear axis;
    a housing mounted to the distal end of the sheath, the housing defining a chamber adapted to contain the medical device, the housing having an open distal port at its distal end;
    an inner shaft extending through the sheath, the inner shaft being inextensible under tension;
    an abutment secured to the distal end of the inner shaft, the abutment being disposed in the chamber and defining the proximal end of the chamber, the inner shaft and abutment being movable longitudinally with respect to the sheath and housing;
    the outer sheath having a shelf adjacent the proximal region of the housing and proximal of the abutment, the shelf being adapted to be engaged by a proximally facing surface of the abutment to apply a compressive load to the outer sheath in response to tensioning of the inner shaft;
    the outer sheath being sufficiently torsionally rigid to transmit, controllably, rotation applied at the proximal end to the distal end;
    the outer sheath being constructed to bend longitudinally away from the linear axis under the compressive load applied by the abutment against the shelf, the degree of bending corresponding to the degree of compression load applied to the sheath; and
    the outer sheath being retractable relative to the abutment whereby a medical device contained in the chamber may be at least partially deployed at a selected location by retracting the outer sheath relative to the abutment.

2. The catheter as defined in claim 1 wherein the outer sheath is constructed to have increasing flexibility in a distal direction.

3. The catheter as defined in claim 2 wherein the outer sheath is formed from a plurality of serially connected segments, the most distal of the segments being the most flexible and exhibiting the greatest degree of longitudinal bending as the sheath is compressed.

4. The catheter as defined in claim 3 wherein the outer sheath has at least three segments including a proximal segment, a shorter intermediate segment and a still shorter distal segment, the housing being relatively inflexible and extending distally from the distal end of the distal segment.

5. The catheter as defined in claim 2 wherein the outer sheath is bendable in response to tensioning of the inner shaft to define an angle of at least about 90 degrees between an axis of the housing and the linear axis.

6. The catheter as defined in claim 2 wherein the outer sheath is bendable in response tensioning the inner shaft to define an angle of at least about 180 degrees between an axis of the housing and the linear axis.

7. The catheter as defined in claim 1 wherein the shelf is defined by the distal end of a distal segment of the sheath, the proximal end of the housing being attached to and about the distal end of the distal segment with the shelf being disposed within the housing.

8. The catheter as defined in claim 7 wherein the shelf is annular and the abutment is in the form of a disc having a diameter to abut the shelf.

9. The catheter as defined in claim 1 wherein the inner shaft includes a lumen extending along its length, the abutment having an aperture in communication with the lumen whereby a tether can extend from a medical device in the chamber to the proximal end of the catheter.

10. The catheter as defined in claim 9 further comprising a clamp at the proximal end of the catheter, the clamp being adapted to receive and releasably clamp the proximal end of the tether.

11. The catheter as defined in claim 1 wherein the abutment is radiopaque to enable the location of the proximal end of the chamber determined fluoroscopically when the chamber is loaded with the medical device.

12. The catheter as defined in claim 11 further comprising a radiopaque marker band located at the distal end of the housing.

13. The catheter as defined in claim 1 further comprising:
a handle at the proximal end of catheter, the handle containing a slide mounted for longitudinal movement, the slide being operable externally of the handle;
the proximal end of the sheath being attached to one of the handle or the slide; and
the proximal end of the inner shaft being attached to the other of the handle or the slide.

14. The catheter as defined in claim 13 further comprising a side port mounted to the handle in communication with the inner shaft to enable fluid communication between the proximal and distal ends of the catheter.

15. A steerable catheter for delivering and deploying a medical device comprising:
a tubular outer sheath having proximal and distal ends;
a housing mounted to the distal end of the sheath, the housing defining a chamber adapted to contain the medical device, the housing having an open distal port at its distal end;
an inner shaft extending through the sheath, the inner shaft being inextensible under tension;
an abutment secured to the distal end of the shaft, the abutment being disposed in the chamber and defining the proximal end of the chamber, the inner shaft and abutment being movable longitudinally with respect to the sheath and the housing;
the outer sheath having a shelf adjacent the proximal region of the housing and proximal of the abutment, the shelf being adapted to be engaged by a proximally facing surface of the abutment and to apply a compressive load to the outer sheath in response to tensioning of the inner shaft;
the outer sheath having means for enabling the sheath to bend longitudinally under the compressive load applied by the abutment against the shelf, the degree of bending corresponding to the degree of compression load applied to the sheath; and the outer sheath being retractable relative to the abutment whereby a medical device contained in the chamber may be at least partially deployed at a selected location by retracting the outer sheath relative to the abutment.

16. A steerable catheter for delivering and deploying a medical device through a femoral vein at least to the right side of a patient's heart comprising:
a tubular outer sheath having proximal and distal ends;
a housing mounted to the distal end of the sheath, the housing defining a chamber adapted to contain the medical device, the housing having an open distal port at its distal end;
an inner shaft extending through the sheath, the inner shaft being inextensible under tension;
an abutment secured to the distal end of the shaft, the abutment being disposed in the chamber and defining the proximal end of the chamber, the inner shaft and abutment being movable longitudinally with respect to the sheath and housing;
the outer sheath having a shelf adjacent the proximal region of the housing and proximal of the abutment, the shelf being adapted to be engaged by a proximally facing surface of the abutment to apply a compressive load to the outer sheath in response to tensioning of the inner shaft;
the outer sheath having means for enabling the sheath to bend longitudinally under the compressive load applied by the abutment against the shelf, the degree of bending corresponding to the degree of compression load applied to the sheath, the sheath being bendable and navigable through a path that includes at least two bends of about 180 degrees; and
the outer sheath being retractable relative to the abutment whereby a medical device contained in the chamber may be at least partially deployed at a selected location by retracting the outer sheath relative to the abutment.

17. The catheter as defined in claim 16 wherein the catheter has a length sufficient to reach the pulmonary artery.

18. A method for delivering and deploying a medical device in the pulmonary artery of a human patient comprising:
receiving a steerable catheter including an elongate tubular outer sheath having proximal and distal ends and a housing mounted to the distal end of the sheath, the housing defining a chamber containing the medical device, the housing having an open distal port at its distal end, the catheter having a inextensible inner shaft extending through the sheath, an abutment secured to the distal end of the inner shaft and being disposed in the chamber and defining the proximal end of the chamber, the inner shaft and abutment being movable longitudinally with respect to the sheath and housing, the outer sheath having a shelf adjacent the proximal region of the housing and proximal of the abutment, the shelf being adapted to be engaged by the proximally facing surface of the abutment and apply a compressive load to the outer sheath in response to tensioning of the inner shaft, the outer sheath being constructed to bend longitudinally under the compressive load applied by the abutment against the shelf, the degree of bending corresponding to the degree of compression load applied to the sheath, the outer sheath being retractable relative to the abutment whereby the medical device contained in the chamber may be at least partially deployed at a selected location by retracting the outer sheath relative to the abutment;
introducing the distal end of the catheter percutaneously into a femoral vein of the patient and advancing the catheter along a path that extends through the right side of the patient's heart and into the pulmonary artery, the path including at least two bends of at least about 180 degrees; and retracting the outer sheath while maintaining the position of the abutment to deploy the medical device.

19. The method for delivering and deploying a medical device as defined in claim 18 wherein advancing the catheter along a path that extends through the right side of the patient's heart and into the pulmonary artery includes tensioning the inner shaft to apply a compressive load to the outer sheath via the abutment and the shelf such that the compression load causes the outer shaft to bend longitudinally.

20. The method for delivering and deploying a medical device as defined in claim 19 wherein advancing the catheter along a path that extends through the right side of the patient's heart and into the pulmonary artery further includes rotating the catheter while causing the outer shaft to bend longitudinally, thereby permitting controllable steering of the distal end of the outer sheath through the path.

* * * * *